United States Patent
Suzuki

(10) Patent No.: US 12,220,478 B2
(45) Date of Patent: Feb. 11, 2025

(54) HAIR COSMETIC COMPOSITION

(71) Applicant: KAO CORPORATION, Tokyo (JP)

(72) Inventor: Ryosuke Suzuki, Kawagoe (JP)

(73) Assignee: KAO CORPORATION, Tokyo (JP)

( * ) Notice: Subject to any disclaimer, the term of this patent is extended or adjusted under 35 U.S.C. 154(b) by 236 days.

(21) Appl. No.: 17/263,397

(22) PCT Filed: Jul. 26, 2019

(86) PCT No.: PCT/JP2019/029459
§ 371 (c)(1),
(2) Date: Jan. 26, 2021

(87) PCT Pub. No.: WO2020/022488
PCT Pub. Date: Jan. 30, 2020

(65) Prior Publication Data
US 2021/0154129 A1    May 27, 2021

(30) Foreign Application Priority Data

Jul. 27, 2018 (JP) ................. 2018-141495

(51) Int. Cl.
| | | |
|---|---|---|
| A61K 8/898 | (2006.01) | |
| A61K 8/34 | (2006.01) | |
| A61K 8/37 | (2006.01) | |
| A61K 8/41 | (2006.01) | |
| A61K 8/43 | (2006.01) | |
| A61K 8/86 | (2006.01) | |
| A61Q 5/00 | (2006.01) | |
| A61Q 5/12 | (2006.01) | |

(52) U.S. Cl.
CPC ............ *A61K 8/898* (2013.01); *A61K 8/34* (2013.01); *A61K 8/345* (2013.01); *A61K 8/347* (2013.01); *A61K 8/37* (2013.01); *A61K 8/41* (2013.01); *A61K 8/43* (2013.01); *A61K 8/86* (2013.01); *A61Q 5/002* (2013.01); *A61Q 5/12* (2013.01)

(58) Field of Classification Search
CPC .................................................... A61K 8/898
See application file for complete search history.

(56) References Cited

U.S. PATENT DOCUMENTS

| | | |
|---|---|---|
| 6,326,011 B1 | 12/2001 | Miyazawa et al. |
| 2005/0196369 A1 | 9/2005 | Ueyama et al. |
| 2008/0175807 A1* | 7/2008 | Aimi ................ A61K 8/64 424/70.1 |
| 2015/0258007 A1 | 9/2015 | Biato et al. |
| 2016/0367459 A1 | 12/2016 | Washington et al. |
| 2019/0160000 A1 | 5/2019 | Herrlein et al. |

FOREIGN PATENT DOCUMENTS

| | | | |
|---|---|---|---|
| CN | 1222185 A | 7/1999 | |
| CN | 1679475 A | 10/2005 | |
| CN | 101909598 A | 12/2010 | |
| EP | 3281623 A1 * | 2/2018 | ........... A61K 8/0204 |
| EP | 3295820 A1 | 3/2018 | |
| JP | 2010-248135 A | 11/2010 | |
| JP | 2011-503059 A | 1/2011 | |
| JP | WO 2009/154269 A1 | 12/2011 | |
| JP | 2014-125448 A | 7/2014 | |
| JP | 2015-013855 A | 1/2015 | |
| JP | 5656638 B2 | 1/2015 | |
| JP | 2016-540005 A | 12/2016 | |
| JP | 2018-517750 A | 7/2018 | |
| JP | 2019-143281 A | 8/2019 | |
| JP | 2019-143282 A | 8/2019 | |
| WO | WO 97/39089 A1 | 10/1997 | |
| WO | WO 98/54255 A1 | 12/1998 | |
| WO | WO 2009/061360 A1 | 5/2009 | |
| WO | WO 2010/116951 A1 | 10/2010 | |
| WO | WO 2017/109146 A1 | 6/2017 | |
| WO | WO 2017/109147 A1 | 6/2017 | |
| WO | WO 2018/115279 A1 | 6/2018 | |

OTHER PUBLICATIONS

Extended European Search Report issued Apr. 7, 2022 in European Patent Application No. 19840901.3, 8 pages.
Anonymous: "SILSOFTCLX-E conditioning agent Specialty Fluids-Personal Care", Internet Citation, Retrieved from the Internet: URL: https://www.momentive.com/en-us/categories/emulisions/silsoft-ctx-e, Nov. 30, 2014 (Nov. 30, 2014), pp. 1-12, XP009528472.
Liquid Umbrella Waterproofing Strands, ID4436531, Mintel GNPD[online], Nov. 2016., [retrieved on Sep. 10, 2019], Retrieved from the Internet : < URL:https://portal.mintel.com>.
International Search Report issued on Sep. 24, 2019 in PCT/JP2019/029459 filed on Jul. 26, 2019, 2 pages.

(Continued)

Primary Examiner — Andrew S Rosenthal
Assistant Examiner — Danielle Kim
(74) Attorney, Agent, or Firm — Oblon, McClelland, Maier & Neustadt, L.L.P.

(57) ABSTRACT

A hair cosmetic composition including components (A) to (C), wherein the content of component (A) is 0.01 to 5.00% by mass and the content of component (B) is 5.00 to 96.77% by mass: (A) an epoxyaminosilane copolymer, which is a reaction product of compounds (a) to (d): (a) a polysiloxane having two or more oxiranyl groups or oxetanyl groups; (b) a polyether having two or more oxiranyl groups or oxetanyl groups; (c) aminopropyltrialkoxysilane; (d) a specific amine; (B) a micelle formation inhibitor selected from (b1) to (b3): (b1) an organic compound having a solubility parameter $\delta_H$ of 10.0 to 15.8 MPa$^{1/2}$, excluding (b3); (b2) a compound selected from ethanol and the like; (b3) an organic salt; (C) water.

3 Claims, No Drawings

(56) References Cited

OTHER PUBLICATIONS

Zhou Yu-peng, et al., "Synthesis of poly(polysiloxane) salt block copolymer and its application in shampoo", Silicone Material, Mar. 27, 2005, 19(2): 26-29 (with a machine-generated English abstract).

Xu Chun-tao, et al., "The Application of Organosilicone Surfactant in Daily Chemical Industry", Flavour Fragrance Cosmetics, No. 4. Aug. 31, 2016, pp. 62-66 (including an English abstract in p. 62).

Barber and Beauty Education Publishing Co., Ltd., "New morning habit 'Chiaro Hairwater', Fiole Cosmetics will be released on Apr. 24", H.B.News, Retrieved from the Internet [URL: http://www.hbnews.ribiyo.co.jp/2018/04/06/fiole-3/], Apr. 6, 2018, Retrieved on Jan. 26, 2024, 7 pages (with unedited computer-generated English translation).

Kabushiki Kaisha Max, "Chiaro Hair Water Fiole Cosmetics", Retrieved from the Internet [URL: http://osaka-mcs.co.jp/%e3%82%ad%e3%82%a2%e3%83%ad%e3%83%98%e3%82%a2%e3%82%a6%e3%82%a9%e3%83%bc%e3%82%bf%e3%83%bc%e3%80%80%e3%83%95%e3%82%a3%e3%83%a8%e3%83%bc%e3%83%ac%e3%82%b3%e3%82%b9%e3%83%a1%e3%83%86%e3%82%a3%e3%82%af.html], May 12, 2018, Retrieved on Jan. 26, 2024, 2 pages (with unedited computer-generated English translation).

Sundrug e-shop Jre Mall, "Fiole CHIARO hair water 150ml", East Japan Railway Company, Retrieved from the Internet [URL: https://www.jreastmall.com/shop/g/gS242-4562210015343/], Retrieved on Jan. 26, 2024, 6 pages (with unedited computer-generated English translation).

Fiole Cosmetics Co., Ltd., "Chiaro Hair Water", Retrieved from the Internet [URL: https://www.fiole.jp/member/catalog_pop/pdf/chiaro_hairwater.pdf], Jan. 2022, Retrieved on Jan. 26, 2024, 4 pages (with unedited computer-generated English translation).

Japan Cosmetic Industry Association, "Guidelines for listing all ingredients of cosmetics (Revised edition)", Retrieved from the Internet [URL: https://www.jcia.org/user/common/download/business/guideline/hlgl.pdf], Feb. 27, 2002, Retrieved on Jan. 26, 2024, 8 pages (with unedited computer-generated English translation).

Hikota, T. et al., "Studies of Ester-Containing Surfactants, The Micelle Formation of Surfactant in Ethanol-Water Mixture", Oil Chemistry, Japan Oil Chemists' Society, vol. 23 No. 3, 1974, 10 pages (with unedited computer-generated English translation).

"Analysis results of Fiole Chiaro Hair Water", Analysta Inc., Shampoo Analysis.com, Retrieved from the Internet [URL: https://www.ishampoo.jp/kaiseki/product/fiolechiarohairwater], Retrieved on Feb. 29, 2024, 9 pages (with unedited computer-generated English translation).

Splash Corporation, "Hair Freshener", Mintel Gnpd, Id#: 5203015, Retrieved from the Internet [URL: https://portal.mintel.com], Oct. 2017, Retrieved on Feb. 29, 2024, 5 pages (with unedited computer-generated English translation).

* cited by examiner

HAIR COSMETIC COMPOSITION

CROSS REFERENCE TO RELATED APPLICATION

This application is a national stage entry under 35 USC 371 of PCT/JP2019/029459, filed on Jul. 26, 2019, and claims priority to Japanese Patent Application No. 2018-141495 filed on Jul. 27, 2018.

FIELD OF THE INVENTION

The present invention relates to a hair cosmetic composition.

BACKGROUND OF THE INVENTION

In recent years, hair ends, in particular, have been seriously damaged due to chemical treatments such as hair colors and perms and hair set or the like using heat from hair irons, hair dryers, etc., which is now becoming common mainly among young women. It has been reported that damaged hair is associated with loss of 18-MEA (18-methyleicosanoic acid), a fatty acid covering the surface of hair, resulting in hydrophilization of the hair surface and an increased surface friction. Symptoms caused by accumulation of such damage, including tangling of hair ends during styling that makes it difficult to create an ideal hair style and poor finger combability are now a serious concern for consumers.

Thus, a technique for recovering hydrophobicity and low friction inherent in healthy hair has been required. Some hair cosmetic compositions which can form a durable polymer coating on the surface of damaged hydrophilic hair to recover lost hydrophobicity have been proposed as an example of such techniques.

For example, Patent Literature 1 discloses a technique in which a copolymer made of (meth)acrylic ester monomers having a silyl group to which a reactive functional group is bonded as a constituent monomer is hydrolyzed and cross-linked on the hair to form a cross-linked coating having excellent resistance to washing.

Furthermore, Patent Literature 2 discloses a technique of forming a hydrophobic coating which is durable against shampooing using a personal care composition comprising a reaction product of a specific oxirane or oxetane compound and a specific amino silane compound (epoxyaminosilane copolymer).

(Patent Literature 1) International Publication No. WO98/54255
(Patent Literature 2) JP-A-2011-503059

SUMMARY OF THE INVENTION

The present invention provides a hair cosmetic composition comprising the following components (A) to (C), wherein the content of component (A) is 0.01% by mass or more and 5.00% by mass or less, and the content of component (B) is 5.00% by mass or more and 96.77% by mass or less:

(A) an epoxyaminosilane copolymer, which is a reaction product of the following compounds (a) to (d):

(a) a polysiloxane having at least two oxiranyl groups or oxetanyl groups;

(b) a polyether having at least two oxiranyl groups or oxetanyl groups;

(c) aminopropyltrialkoxysilane; and (d) a compound selected from the group consisting of the following primary and secondary amines:

primary amines: methylamine, ethylamine, propyleneamine, ethanolamine, isopropylamine, butylamine, isobutylamine, hexylamine, dodecylamine, oleylamine, aniline, aminopropyltrimethylsilane, aminopropyltriethylsilane, aminomorpholine, aminopropyldiethylamine, benzylamine, naphthylamine, 3-amino-9-ethylcarbazole, 1-aminoheptafluorohexane, and 2,2,3,3,4,4,5,5,6,6,7,7,8,8,8-pentadecafluoro-1-octanamine; and secondary amines: methylethylamine, methyloctadecylamine, diethanolamine, dibenzylamine, dihexylamine, dicyclohexylamine, piperidine, pyrrolidine, phthalimide, and polymeric amines;

(B) a micelle formation inhibitor comprising at least one selected from the following (b1) to (b3):

(b1) an organic compound having a hydrogen bond term of the Hansen solubility parameter of 10.0 $MPa^{1/2}$ or more and 15.8 $MPa^{1/2}$ or less (excluding those corresponding to (b3));

(b2) a compound selected from ethanol, triethylene glycol, pentylene glycol, methyl propanediol, diethanolamine and N-methyldiethanolamine; and (b3) an organic salt; and (C) water.

DETAILED DESCRIPTION OF THE INVENTION

In the technique described in Patent Literature 1, the composition needs to be separated from water before use in order to prevent the copolymer from being cross-linked during storage. Thus, a hydrolyzation step for cross-linking must be performed immediately before use, and this cannot be said to be convenient for consumers.

Furthermore, although the technique described in Patent Literature 2 is more convenient, durability against washing is achieved only through a process in which hair is subjected to an immersion treatment at a high bath ratio and dried for enough time, and thus no effect is obtained in a leave-on treatment with a low bath ratio. Accordingly, this does not meet recent consumers' demand to have effects in a simple, short-time treatment using a small amount of compositions.

Accordingly, the present invention relates to a hair cosmetic composition which gives sufficient hydrophobicity and has friction-lowering effects when hair is treated therewith for a short time at a low bath ratio and which can maintain such effects for a long time after the treatment.

The present inventors have conducted intensive studies and have found that the above problem can be solved by suppressing formation of micelles in a hair cosmetic composition containing an epoxyaminosilane copolymer, and have completed the present invention.

[Component (A): Epoxyaminosilane Copolymer]

The epoxyaminosilane copolymer of component (A) is a reaction product of the components (a) to (d) described below.

<Compounds (a) and (b)>

The compound (a) is a polysiloxane having at least two oxiranyl groups or oxetanyl groups. Examples thereof include those represented by the following formula (1):

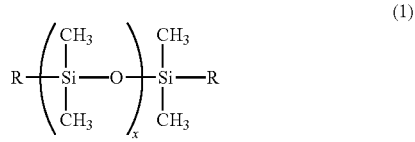

wherein R represents a hydrocarbon group having 1 to 6 carbon atoms and having an oxiranyl group or an oxetanyl group at the terminal thereof and optionally having a heteroatom, and x represents a number of from 1 to 1,000.

The compound (b) is a polyether having at least two oxiranyl groups or oxetanyl groups. Examples thereof include those represented by the following formula (2):

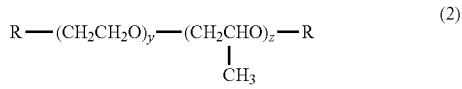

wherein R is as defined above, y represents a number of from 1 to 100, z represents a number of from 0 to 100, and y+z is 1 to 200.

In the formulas (1) and (2), an oxygen atom is preferred as the heteroatom which R optionally has. Examples of R include an oxiranylmethyl group (glycidyl group), an oxiranylmethoxy group (glycidyloxy group), an oxiranylmethoxypropyl group (glycidyloxypropyl group), an oxetanylmethyl group, an oxetanylmethoxy group, an oxetanylmethoxypropyl group and a 3-ethyloxetanylmethyl group. In particular, a hydrocarbon group having 1 to 4 carbon atoms and an oxiranyl group and optionally having an oxygen heteroatom is preferred, and at least one selected from an oxiranylmethyl group (glycidyl group), an oxiranylmethoxy group (glycidyloxy group) and an oxiranylmethoxypropyl group (glycidyloxypropyl group) is more preferred.

<Compound (c)>

The compound (c) is aminopropyltrialkoxysilane. Examples of alkoxy groups in the compound (c) include those having 1 to 6 carbon atoms. Those having 2 to 4 carbon atoms are preferred and those having 3 carbon atoms are more preferred, and an isopropoxy group is particularly preferred. Examples of compounds (c) include aminopropyltrimethoxysilane, aminopropyltriethoxysilane, aminopropyltripropoxysilane, aminopropyltriisopropoxysilane, aminopropyltributoxysilane and aminopropyltritert-butoxysilane. Among them, aminopropyltriisopropoxysilane is preferred. For compound (c), one of these may be used alone, or two or more of them may be used in combination.

<Compound (d)>

The compound (d) is a compound selected from the group consisting of the following primary and secondary amines: primary amines: methylamine, ethylamine, propyleneamine, ethanolamine, isopropylamine, butylamine, isobutylamine, hexylamine, dodecylamine, oleylamine, aniline, aminopropyltrimethylsilane, aminopropyltriethylsilane, aminomorpholine, aminoethyldimethylamine, aminoethyldiethylamine, aminoethyldibutylamine, aminopropyldimethylamine, aminopropyldiethylamine, aminopropyldibutylamine, benzylamine, naphthylamine, 3-amino-9-ethylcarbazole, 1-aminoheptafluorohexane, and 2,2,3,3,4,4,5,5,6,6,7,7,8,8,8-pentadecafluoro-1-octanamine; and secondary amines: methylethylamine, methyloctadecylamine, diethanolamine, dibenzylamine, dihexylamine, dicyclohexylamine, piperidine, pyrrolidine, phthalimide, and polymeric amines.

Among them, primary amines are preferred, and at least one selected from aminopropyldiethylamine, aminopropyldimethylamine and aminopropyldibutylamine is more preferred. For compound (d), one of these may be used alone, or two or more of them may be used in combination.

The reaction of the compounds (a) to (d) is performed under reflux in a solvent such as isopropanol for a predetermined time. The molar ratio of the oxiranyl groups or the oxetanyl groups in the compound (a) and (b) to the amino group in the compound (c) is preferably 1 or more, more preferably 1.1 or more, and further preferably 1.2 or more, and preferably 4 or less, more preferably 3.9 or less, and further preferably 3.8 or less.

Examples of components (A) include those with the INCI name of Polysilicone-29, and examples of commercially available products thereof include Silsoft CLX-E (15% by mass of active amount, containing dipropylene glycol and water) manufactured by Momentive Performance Materials.

The epoxyaminosilane copolymer of component (A) has two characteristics. The first one is that the compound forms molecular aggregates (micelles) in water, since the compound has a hydrophobic polysiloxane moiety and a hydrophilic polyether moiety, and thus is capable of forming micelles; and the second one is that the compound includes, as a structural unit thereof, a structural unit derived from aminopropyltrialkoxysilane.

The present inventors have purposely suppressed the ability to form micelles which is the first characteristic of the epoxyaminosilane copolymer, more specifically, the inventors have added an agent which inhibits the ability to form micelles (component (B)) to use the composition as a hair cosmetic composition, and then the inventors surprisingly found that the composition gives sufficient hydrophobicity and friction-lowering effects by treating hair with the composition for a short time at a low bath ratio, and such effects can be maintained for a long time after the treatment.

Although details of the cause are not clear, the present inventors have presumed it as follows: suppression of formation of micelles in an aqueous solution containing component (A) increases the solubility of the epoxyaminosilane copolymer of component (A), facilitating adsorption to hair to achieve homogenous attachment and reduce the time of drying. Furthermore, since molecules of epoxyaminosilane polymer attached to hair are cross-linked to each other by the reaction of silanol, which is a structural unit derived from aminopropyltrialkoxysilane, in the drying step after adsorption, a high molecular weight silicone is attached to the hair. Such a high molecular weight silicone is attached to the hair at a plurality of portions due to the interaction with the hair, and thus the hair becomes hydrophobic.

The content of component (A) in the hair cosmetic composition of the present invention is 0.01% by mass or more, preferably 0.05% by mass or more, more preferably 0.10% by mass or more, and further preferably 0.20% by mass or more to give sufficient hydrophobicity to hair. To avoid giving sticky feeling, the content is 5.00% by mass or less, preferably 4.00% by mass or less, more preferably 3.00% by mass or less, and further preferably 2.00% by mass or less.

[Component(B): Micelle Formation Inhibitor]

The micelle formation inhibitor of component (B) used in the present invention is a compound which is capable of suppressing formation of micelles in an aqueous solution containing component (A). The effect of inhibiting formation of micelles of the compound is measured by the method described in The Journal of Physical Chemistry B, 2002, 106, 10845-10853, Self-Assembly of an Amphiphilic Siloxane Graft Copolymer in Water. The polyether modified silicone described later should be used as the reagent. More specifically, the effect of inhibiting formation of micelles of a compound can be determined by actually measuring the critical micelle concentration (CMC) when the compound is added to an aqueous solution of polyether modified silicone at a fixed concentration. Since the epoxyaminosilane copolymer of component (A) is also a polyether modified silicone derivative, a compound which increases the CMC of an aqueous solution of polyether modified silicone measured by the above method compared to the CMC in the absence of the compound can be said to be a compound that suppresses formation of micelles in the aqueous solution of component (A). In other words, the micelle formation inhibitor of component (B) according to the present invention refers to a compound which increases the CMC of an aqueous solution of polyether modified silicone measured by the following procedure compared to the CMC in the absence of the compound (0.13% by mass), preferably to 0.20% by mass or more.

It is preferable that the value of CMC of the aqueous solution of polyether modified silicone described above be high from the viewpoint of suppression of formation of micelles in the epoxyaminosilane copolymer of component (A) to facilitate adsorption to hair, give sufficient hydrophobicity and friction-lowering effects in a short time and maintain these effects for a long time after the treatment.

(Reagents Used)
Polyether modified silicone: KF-6011 (PEG-11 methyl ether dimethicone, HLB 14.5, manufactured by Shin-Etsu Chemical Co., Ltd.)
Labeled compound: 1,6-diphenylhexa-1,3,5-triene (manufactured by Kanto Chemical Industry, Co., Ltd.)
(Experimental Procedure)
1. An aqueous solution containing 1% by mass, 5% by mass or 10% by mass of a compound to be evaluated for the effect of inhibiting formation of micelles (the highest concentration of them, at which the compound is soluble) depending on their solubility, and 0.01 to 0.80% by mass of polyether modified silicone is prepared.
2. A methanol solution of the labeled compound at a concentration of 0.4 mM is separately prepared.
3. 5.0 mL of the solution prepared in step 1 and 50 μL of the methanol solution prepared in step 2 are mixed and left overnight.
4. Ultraviolet-visible absorption is measured.
5. The absorbance at 354 nm is plotted on the vertical axis and the concentration of polyether modified silicone is plotted on the horizontal axis.
6. The concentration of polyether modified silicone at which the absorbance starts to increase is determined as the critical micelle concentration (CMC).

(Measurement Equipment)
JASCO V-560 UV-VIS Spectrometer manufactured by JASCO Corporation.
(Measurement Conditions)
Measurement range: 300 nm to 400 nm
Temperature: 25° C.
Cell: PMMA disposable cell, outer dimensions (mm) 12.5×12.5×45H (manufactured by Brand)

Examples of the micelle formation inhibitor of component (B) which meets the above conditions include: (b1) an organic compound having a hydrogen bond term of the Hansen solubility parameter of 10.0 $MPa^{1/2}$ or more and 15.8 $MPa^{1/2}$ or less (excluding the compounds corresponding to (b3)); (b2) a compound selected from ethanol, triethylene glycol, pentylene glycol, methylpropanediol, diethanolamine and N-methyldiethanolamine; and (b3) an organic salt. In the present invention, the hydrogen bond term of the Hansen solubility parameter refers to $\delta_H$ ($MPa^{1/2}$) (energy term for intermolecular hydrogen bonds) calculated using a software package HSPiP 4th Edition 4.1.07 according to Hansen Solubility Parameters: A User's Handbook, CRC Press, Boca Raton FL, 2007, in DIY program at 25° C.

Examples of the organic compound having a hydrogen bond term of the Hansen solubility parameter of 10.0 $MPa^{1/2}$ or more and 15.8 $MPa^{1/2}$ or less (b1) of component (B) include organic compounds such as an aliphatic alcohol having a linear or branched alkyl group having 2 or more and 8 or less carbon atoms and one or more hydroxyl groups, an aromatic alcohol, an ether alcohol, an N-alkylpyrrolidone, an acyclic ester and an alkylamine optionally having a hydroxyl group.

Specific examples of compounds having a hydrogen bond term of the Hansen solubility parameter of 10.0 $MPa^{1/2}$ or more and 15.8 $MPa^{1/2}$ or less will be described below. Numbers in parentheses for the respective examples represent the hydrogen bond term calculated by the above method.

Examples of aliphatic alcohols having a linear or branched alkyl group having 2 or more and 8 or less carbon atoms and one or more hydroxyl groups: a lower alkanol such as 1-propanol (14.7), 2-propanol (14.3), 1-butanol (15.2) and 2-butanol (12.4); a polyhydric alcohol such as hexylene glycol (15.0), octanediol (14.5) and decanediol (12.8)

Examples of aromatic alcohols: benzyl alcohol (12.4), cinnamyl alcohol (10.9), phenethyl alcohol (11.4), p-anisyl alcohol (12.1), p-methylbenzyl alcohol (11.2), phenoxyethanol (12.2), 2-benzyloxyethanol (10.8) and 2-phenyl-1-propanol (10.2)

Examples of ether alcohols: ethylene glycol monoethyl ether (15.7), ethylene glycol monobutyl ether (13.0), diethylene glycol monomethyl ether (13.1), diethylene glycol monoethyl ether (11.9), diethylene glycol monobutyl ether (11.7) and ethylhexyl glyceryl ether (13.1)

Examples of N-alkylpyrrolidones: N-(2-hydroxyethyl)-2-pyrrolidone (13.5)

Examples of acyclic esters: ethyl lactate (14.4) and butyl lactate (11.9)

Examples of alkylamines optionally having a hydroxyl group: methylamine (13.0), ethylamine (10.2), N,N-dimethylmonoethanolamine (13.1) and aminomethylpropanol (14.4)

Among them, those having a hydrogen bond term of the Hansen solubility parameter of 15.5 $MPa^{1/2}$ or less are preferred, those having that of 15.0 $MPa^{1/2}$ or less are more preferred, those having that of 13.0 $MPa^{1/2}$ or less are further preferred, and those having that of 12.5 $MPa^{1/2}$ or less are further preferred from the viewpoint of exerting ability to inhibit formation of micelles. Those having a hydrogen bond term of the Hansen solubility parameter of 10.5 $MPa^{1/2}$ or more are preferred, those having that of 11.0 $MPa^{1/2}$ or more are more preferred, those having that of 11.5 $MPa^{1/2}$ or more are further preferred, and those having that of 12.0 $MPa^{1/2}$ or more are further preferred from the same point of view.

In particular, an aromatic alcohol and an ether alcohol are preferred, and at least one selected from benzyl alcohol (12.4), phenethyl alcohol (11.4), phenoxyethanol (12.2) and 2-benzyloxyethanol (10.8) is more preferred.

The compound selected from ethanol, triethylene glycol, pentylene glycol, methylpropanediol, diethanolamine and N-methyldiethanolamine (b2) of component (B) has the ability to inhibit formation of micelles, although having a hydrogen bond term of the Hansen solubility parameter of more than 15.8 $MPa^{1/2}$.

At least one selected from a guanidine salt having a guanidinium group and an arginine salt is preferred as the organic salt (b3) of component (B). Examples of guanidine salts include at least one selected from guanidine hydrochloride salt, guanidine nitrate salt, guanidine phosphate salt, guanidine thiocyanate salt, guanidine carbonate salt, guanidine acetate salt, guanidine sulfate salt, guanidine sulfamate salt, aminoguanidine hydrochloride salt and aminoguanidine sulfate salt. Examples of arginine salts include at least one selected from arginine hydrochloride salt, arginine nitrate salt, arginine phosphate salt, arginine thiocyanate salt, arginine carbonate salt, arginine acetate salt, arginine sulfate salt, arginine sulfamate salt, arginine glutamate salt and arginine aspartate salt.

One of the components (B) may be used alone, or two or more of them may be used in combination. For example, benzyl alcohol and phenethyl alcohol may be selected from (b1) and used in combination, or benzyl alcohol may be selected from (hi) and ethanol may be selected from (b2) and used in combination. The total amount of (b1) and (b2) in component (B) is preferably 90% by mass or more, more preferably 95% by mass or more, further preferably 98% by mass or more, and further preferably substantially 100% by mass from the viewpoint of improving the feeling in use.

More specifically, component (B) is preferably at least one selected from ethanol, benzyl alcohol, triethylene glycol, pentylene glycol, methyl propanediol, phenoxyethanol, ethyl lactate, diethanolamine and a guanidine salt, more preferably at least one selected from ethanol, benzyl alcohol, phenoxyethanol, ethyl lactate, diethanolamine and a guanidine salt, and further preferably at least one selected from ethanol, benzyl alcohol and phenoxyethanol from the viewpoint of suppression of formation of micelles in the epoxyaminosilane copolymer of component (A) to facilitate adsorption to hair, give sufficient hydrophobicity and friction-lowering effects in a short time and maintain these effects for a long time after the treatment.

The content of component (B) in the hair cosmetic composition of the present invention is 5.00% by mass or more, preferably 6.00% by mass or more, more preferably 7.00% by mass or more, further preferably 10.0% by mass or more, still more preferably 12.0% by mass or more, and yet more preferably 15.0% by mass or more from the viewpoint of maintaining the effect of giving hydrophobicity to hair and the effect of lowering friction for a long time. In addition, the content is 96.77% by mass or less, preferably 95.0% by mass or less, more preferably 90.0% by mass or less, further preferably 80.0% by mass or less, still more preferably 70.0% by mass or less, and yet more preferably 60.0% by mass or less from the viewpoint of improving storage stability.

The mass ratio of component (B) to component (A), (B)/(A), is preferably 1 or more, more preferably 5 or more, further preferably 6 or more, and still more preferably 7 or more from the viewpoint of producing a sufficient effect of inhibiting formation of micelles. In addition, the mass ratio is preferably 2,000 or less, more preferably 1,000 or less, further preferably 500 or less, and still more preferably 200 or less from the viewpoint of improving storage stability.

[Component (C): Water]

The content of water of component (C) in the hair cosmetic composition of the present invention is preferably 10% by mass or more, more preferably 15% by mass or more, further preferably 20% by mass or more from the viewpoint of facilitating application to hair. In addition, the content is preferably 90% by mass or less, more preferably 85% by mass or less, and further preferably 80% by mass or less from the viewpoint of facilitating drying of hair after the application.

[Thickener]

The hair cosmetic composition of the present invention may also contain a thickener. Examples of thickeners include an anionic thickener, a cationic thickener and a nonionic thickener.

Specific examples of anionic thickeners include a polyacrylic acid (Carbopol 941, ditto 981 manufactured by Noveon), an acrylic acid alkyl methacrylate copolymer (Carbopol ETD 2020 manufactured by Noveon), a hydrolysate of a lower alkyl vinyl ether/maleic anhydride copolymer partially cross-linked with a terminal-unsaturated diene compound, or a monoalkyl ester thereof (Stabilieze 06, ditto QM manufactured by ASHLAND), carrageenan (e.g., SOAGEENA LX22, ditto ML210 manufactured by Mitsubishi Rayon, Co., Ltd.), xanthan gum (Echo gum T manufactured by Sumitomo Dainippon Pharma Co., Ltd.), welan gum (e.g., K1C376, K1A96 manufactured by Sansho Co., Ltd.), hydroxypropyl xanthan gum (e.g., Rhaball gum EX manufactured by Sumitomo Dainippon Pharma Co., Ltd.), sodium stearoxy PG-hydroxyethylcellulose sulfonate and a hydroxyethyl acrylate/sodium acryloyldimethyl taurine) copolymer (e.g., SIMULGEL NS, SEPINOV EMT10 manufactured by SEPPIC).

Examples of cationic thickeners include natural or semi-synthetic cationic polysaccharides and synthetic polymers having an amino group or an ammonium group in the side chain of polymer chains, or having a diallyl quaternary ammonium salt as a structural unit.

Specific examples of cationic polysaccharides include cationized cellulose derivatives (e.g., LEOGARD G, ditto GP manufactured by Lion Corporation, UCARE polymer JR-125, ditto JR-400, JR-30M, LR-400, LR-30M manufactured by The Dow Chemical Company, CELQUAT H-100, ditto L-200 manufactured by AkzoNovel), cationized guar gum derivatives (e.g., JAGUAR C-13S, ditto C-17 manufactured by Solvay, Rabole gum CG-M, ditto CG-M7, CG-M8M manufactured by DSP GOKYO FOOD & CHEMICAL Co., Ltd.), hydroxypropyl chitosan (e.g. Chitofilmer HV-10 manufactured by ICHIMARU PHARCOS) and chitosan•dl-pyrrolidone carboxylate (e.g., KYTAMER manufactured by Union Carbide Corporation).

Examples of synthetic cationic polymers having an amino group or an ammonium group in the side chain of polymer chains include a synthetic cationic polymer containing trialkylaminoalkyl (meth)acrylate, trialkylaminoalkyl (meth)acrylamide, (meth)acrylamide, or vinylamine as a structural unit. Specific examples thereof include poly(ethyltrimonium chloride methacrylate) (INCI name: Polyquaternium-37, e.g., Cosmedia Ultragel 300 manufactured by BASF), an (acrylic acid/methyl acrylate/3-methacryloylaminopropyl trimethylammonium chloride) copolymer (INCI Name: Polyquaternium-47, e.g., Merquat 2201 manufactured by Lubrizol), an (acrylic acid/acrylamide/methylmethacrylamidopropyltrimethylammonium chloride) copolymer (INCI Name: Polyquaternium-53, e.g., Merquat 2003 manufactured by Lubrizol), a (dimethylacrylamide/ethyl methacrylate trimonium chloride) copolymer (e.g., Tinobis CD manufactured by BASF), and a (vinyl amine/vinyl alcohol) copolymer (e.g., SEVOL ULTALUX AD manufactured by Sekisui Specialty Chemicals, Diafix C-601 manufactured by Mitsubishi Chemical Corporation).

Specific examples of synthetic cationic polymers having a diallyl quaternary ammonium salt as a structural unit include a polymer of diallyl dimethyl ammonium chloride (INCI Name: Polyquaternium-6, e.g., Merquat 100 manufactured by Lubrizol), a (dimethyldiallylammonium chloride/acrylamide) copolymer (INCI: Polyquaternium-7, e.g., Merquat 550, ditto 740 manufactured by Lubrizol), an (acrylic acid/diallyl dimethyl ammonium chloride) copolymer (INCI Name: Polyquaternium-22, e.g., Merquat 280, ditto 295 manufactured by Lubrizol) and an (acrylamide/acrylic acid/diallyl dimethyl ammonium chloride) copolymer (INCI Name: Polyquaternium-39, e.g., Merquat Plus 3330, ditto 3331 manufactured by Lubrizol).

Examples of nonionic thickening polymers include natural or semi-synthetic nonionic polysaccharides and synthetic nonionic polymers having vinyl alcohol or oxyalkylene as a structural unit.

Specific examples of natural or semi-synthetic nonionic polysaccharides include water-soluble natural polysaccharides such as starch, guar gum, locust bean gum and glucomannan, and water-soluble hydroxyalkylated polysaccharides prepared by reacting an alkylene oxide with cellulose, starch, guar gum, locust bean gum or the like. Specific examples thereof include guar gum (e.g., Fiberon S manufactured by DSP GOKYO FOOD & CHEMICAL Co., Ltd.) and pullulan (pullulan PI-20 manufactured by Hayashibara Co., Ltd.). Examples include hydroxyethylcellulose (e.g. SE-850 manufactured by DAICEL FINECHEM Ltd., CELLOSIZE HEC QP-52000-H manufactured by The Dow Chemical Company), methyl hydroxyethylcellulose (STRUCTURE CELL 12000M manufactured by AkzoNovel), hydroxypropylcellulose (e.g.

HPC-H, ditto HPC-M, HPC-L manufactured by NIPPON SODA CO., LTD.) and hydroxypropyl methylcellulose (e.g. METOLOSE 60SH-10000 manufactured by Shin-Etsu Chemical Co., Ltd.).

Specific examples of synthetic nonionic thickening polymers having vinyl alcohol or oxyalkylene as a structural unit include polyvinyl alcohol (e.g., GOHSENOL EG-40, ditto GH-05, KH-20, NH-26 manufactured by The Nippon Synthetic Chemical Co., Ltd.), a highly polymerized polyethylene glycol (e.g., POLYOX WSR N-60K, ditto WSR301, WSR303 manufactured by The Dow Chemical Company) and a (PEG-240/decyltetradeceth-20/HDI) copolymer (e.g., ADEKA NOL GT-700 manufactured by ADEKA Corporation).

One of these thickeners may be used alone, or two or more of them may be used in combination. The content of the thickener in the hair cosmetic composition of the present invention is preferably 0.01% by mass or more, more preferably 0.05% by mass or more, and further preferably 0.10% by mass or more, and preferably 5.0% by mass or less, more preferably 3.0% by mass or less, and further preferably 1.0% by mass or less from the viewpoint of appropriate and easy application to hair.

[pH Adjuster]

The pH of the hair cosmetic composition of the present invention is preferably in the following range from the viewpoint of an increase in the reaction rate of the trialkoxysilane moiety of component (A) in the acidic region or the basic region. When the pH of the hair cosmetic composition of the present invention is in the acidic region, the pH is preferably 1 or more, more preferably 1.5 or more, and further preferably 2 or more, and preferably 5 or less, more preferably 4.0 or less, and further preferably 3.5 or less. Furthermore, when the pH of the hair cosmetic composition of the present invention is in the basic region, the pH is preferably 7 or more, more preferably 7.5 or more, and further preferably 8.0 or more, and preferably 11 or less, more preferably 10.5 or less, and further preferably 10 or less. To adjust the pH of the hair cosmetic composition of the present invention to the above range, the hair cosmetic composition of the present invention may contain a pH adjuster as necessary. An alkali agent including alkanolamines such as monoethanolamine, isopropanolamine, 2-amino-2-methylpropanol and 2-aminobutanol, or a salt thereof; alkanediamines such as 1,3-propanediamine, or a salt thereof; carbonates such as guanidine carbonate, sodium carbonate, potassium carbonate, sodium hydrogen carbonate and potassium hydrogen carbonate; and hydroxides such as sodium hydroxide and potassium hydroxide may be used as the pH adjuster. Furthermore, acidic agents such as inorganic acids such as hydrochloric acid and phosphoric acid, hydrochlorides such as monoethanolamine hydrochloride; phosphates such as potassium dihydrogen phosphate and disodium hydrogen phosphate, and organic acids such as lactic acid and malic acid may be used.

[Optional Components]

The hair cosmetic composition of the present invention may also contain, in addition to the above components, a component usually blended in a hair cosmetic composition. Examples thereof include an anti-dandruff agent; a vitamin preparation; a microbicide; an anti-inflammatory agent; an antiseptic; a chelating agent; a moisturizer; a colorant such as a dye or a pigment; extracts; a pearling agent; a perfume; an ultraviolet absorber; an antioxidant; a photocatalyst; shea butter; rose water; sunflower oil; orange oil; *eucalyptus* oil; and a surfactant. Examples of photocatalysts include metal oxides such as titanium oxide and tungsten oxide, aromatic hydroxy compounds such as 8-hydroxyquinoline, 7-cyano-2-naphthol and 8-quinolinol-1-oxide, sulfonated pyrene compounds, onium salts, diazomethane derivatives, bissulfone derivatives, disulfono derivatives, nitrobenzyl sulfonate derivatives, sulfonic acid ester derivatives, and a sulfonic acid ester of N-hydroxyimide. Any one of a cationic surfactant, an anionic surfactant, an amphoteric surfactant and a nonionic surfactant may be used as the surfactant. Examples of cationic surfactants include an alkylamine salt and an alkyl quaternary ammonium salt. Examples of anionic surfactants include an alkyl sulfonate, an alkyl carboxylate, an alkyl ether sulfonate and an alkyl ether carboxylate. Examples of amphoteric surfactants include imidazoline, carbobetaine, amidobetaine, sulfobetaine, hydroxysulfobetaine and amidosulfobetaine. Examples of nonionic surfactants include esters such as a glycerol fatty acid ester, a sorbitan fatty acid ester and a sucrose fatty acid ester, and ethers such as a polyoxyethylene alkyl ether, a polyoxyethylene alkylphenyl ether, a polyoxyethylene·polyoxypropylene alkyl ether and polyoxyethylene·polyoxypropylene alkyl phenyl ether.

More specifically, polyols such as propylene glycol, dipropylene glycol and glycerol may be used for the purpose of, for example, moisturization. The content of these components in the hair cosmetic composition of the present invention is preferably 20% by mass or less, more preferably 10% by mass or less, and further preferably 5% by mass or less. The amount of the photocatalyst in the hair cosmetic composition of the present invention is preferably 2% by mass or less, more preferably 1% by mass or less, further preferably 0.1% by mass or less, and still more preferably substantially 0% by mass from the viewpoint of maintaining storage stability of the cosmetic composition. The amount of the surfactant in the hair cosmetic composition of the present invention is preferably 2% by mass or less, more preferably 1% by mass or less, further preferably 0.1% by mass or less, and still more preferably substantially 0% by mass from the viewpoint of maintaining persistent effects.

[Dosage Form and the Like]

The dosage form of the hair cosmetic composition of the present invention may be, for example, a liquid, an emulsion, a cream, a gel, a paste, a mousse, an aerosol. The dosage form is preferably a liquid, a gel, a paste, a mousse and an aerosol from the viewpoint of increasing the drying rate to promote formation of coating. If the dosage form is an aerosol, the content of each component described above and the pH of the hair cosmetic composition mean the content of each component in a stock solution not containing a propellant and the pH of the stock solution, respectively.

[Method of Use]

The hair cosmetic composition of the present invention may be used by a method in which the composition is rinsed off after being applied to hair, or a method in which the composition is applied to hair and dried without being rinsed off. It is preferable that the composition be used by the method in which the composition is applied to hair and then dried without being rinsing off in order to increase the effect of the present invention.

The amount of the hair cosmetic composition of the present invention to be applied to hair is determined relative to the mass of the hair so that the bath ratio (the mass of the hair cosmetic composition/the mass of the hair) is preferably 0.001 or more, more preferably 0.005 or more, and further preferably 0.01 or more, and preferably 100 or less, more preferably 10 or less, and further preferably 1 or less.

For the embodiment described above, preferred aspects of the present invention will be further disclosed.

<1>

A hair cosmetic composition comprising the following components (A) to (C), wherein the content of component (A) is 0.01% by mass or more and 5.00% by mass or less, and the content of component (B) is 5.00% by mass or more and 96.77% by mass or less:

(A) an epoxyaminosilane copolymer, which is a reaction product of the following compounds (a) to (d):
(a) a polysiloxane having at least two oxiranyl groups or oxetanyl groups;
(b) a polyether having at least two oxiranyl groups or oxetanyl groups;
(c) aminopropyltrialkoxysilane; and
(d) a compound selected from the group consisting of the following primary and secondary amines:
primary amines: methylamine, ethylamine, propyleneamine, ethanolamine, isopropylamine, butylamine, isobutylamine, hexylamine, dodecylamine, oleylamine, aniline, aminopropyltrimethylsilane, aminopropyltriethylsilane, aminomorpholine, aminopropyldiethylamine, benzylamine, naphthylamine, 3-amino-9-ethylcarbazole, 1-aminoheptafluorohexane, and 2,2,3,3,4,4,5,5,6,6,7,7,8,8,8-pentadecafluoro-1-octanamine; and
secondary amines: methylethylamine, methyloctadecylamine, diethanolamine, dibenzylamine, dihexylamine, dicyclohexylamine, piperidine, pyrrolidine, phthalimide, and polymeric amines;

(B) a micelle formation inhibitor comprising at least one selected from the following (b1) to (b3):
(b1) an organic compound having a hydrogen bond term of the Hansen solubility parameter of 10.0 $\text{MPa}^{1/2}$ or more and 15.8 $\text{MPa}^{1/2}$ or less (excluding those corresponding to (b3));
(b2): a compound selected from ethanol, triethylene glycol, pentylene glycol, methyl propanediol, diethanolamine and N-methyldiethanolamine; and
(b3): an organic salt; and
(C) water.

<2>

The hair cosmetic composition according to <1>, wherein compound (a) is preferably a compound represented by the following formula (1):

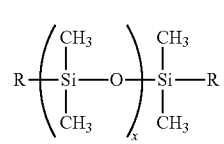

wherein R represents a hydrocarbon group having 1 to 6 carbon atoms and having an oxiranyl group or an oxetanyl group at the terminal thereof and optionally having an oxygen heteroatom, and x represents a number of from 1 to 1,000.

<3>

The hair cosmetic composition according to <1> or <2>, wherein compound (b) is preferably a compound represented by the following formula (2):

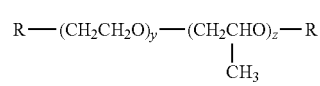

wherein R is as defined above, y represents a number of from 1 to 100, z represents a number of from 0 to 100, and y+z is 1 to 200.

<4>

The hair cosmetic composition according to <2> or <3>, wherein R is preferably at least one selected from an oxiranylmethyl group (glycidyl group), an oxiranylmethoxy group (glycidyloxy group), an oxiranylmethoxypropyl group (glycidyloxy propyl group), an oxetanylmethyl group, an oxetanylmethoxy group, an oxetanylmethoxypropyl group and a 3-ethyloxetanylmethyl group, and more preferably at least one selected from an oxiranylmethyl group (glycidyl group), an oxiranylmethoxy group (glycidyloxy group) and an oxiranylmethoxypropyl group (glycidyloxy propyl group).

<5>

The hair cosmetic composition according to any one of <1> to <4>, wherein the alkoxy group in compound (c) is preferably an alkoxy group having 1 to 6 carbon atoms, more preferably an alkoxy group having 2 to 4 carbon atoms, further preferably an alkoxy group having 3 carbon atoms, and still more preferably an isopropoxy group.

<6>

The hair cosmetic composition according to any one of <1> to <4>, wherein compound (c) is preferably selected from aminopropyltrimethoxysilane, aminopropyltriethoxysilane, aminopropyltripropoxysilane, aminopropyltriisopropoxysilane, aminopropyltributoxysilane and aminopropyltri-tert-butoxysilane, and compound (c) is more preferably aminopropyltriisopropoxysilane.

<7>

The hair cosmetic composition according to any one of <1> to <6>, wherein compound (d) is preferably a primary amine, and more preferably at least one selected from aminopropyldiethylamine, aminopropyldimethylamine and aminopropyldibutylamine.

<8>

The hair cosmetic composition according to any one of <1> to <7>, wherein component (A) is preferably polysilicone-29.

<9>

The hair cosmetic composition according to any one of <1> to <8>, wherein the content of component (A) in the hair cosmetic composition is preferably 0.05% by mass or more, more preferably 0.10% by mass or more, and further preferably 0.20% by mass or more, and preferably 4.00% by mass or less, more preferably 3.00% by mass or less, and further preferably 2.00% by mass or less.

<10>

The hair cosmetic composition according to any one of <1> to <9>, wherein (b1) comprises at least one selected from an organic compound having a hydrogen bond term of the Hansen solubility parameter of preferably 15.5 MPa$^{1/2}$ or less, more preferably 15.0 MPa$^{1/2}$ or less, further preferably 13.0 MPa$^{1/2}$ or less, and still more preferably 12.5 MPa$^{1/2}$ or less, and preferably 10.5 MPa$^{1/2}$ or more, more preferably 11.0 MPa$^{1/2}$ or more, further preferably 11.5 MPa$^{1/2}$ or more, and still more preferably 12.0 MPa$^{1/2}$ or more.

<11>

The hair cosmetic composition according to <10>, wherein (b1) is preferably at least one organic compound selected from the group consisting of an aliphatic alcohol having a linear or branched alkyl group having 2 or more and 8 or less carbon atoms and one or more hydroxyl groups, an aromatic alcohol, an ether alcohol, an N-alkylpyrrolidone, an acyclic ester and an alkylamine optionally having a hydroxyl group.

<12>

The hair cosmetic composition according to <10> or <11>, wherein (b1) is preferably an aromatic alcohol or an ether alcohol, and more preferably at least one selected from benzyl alcohol, phenethyl alcohol, phenoxyethanol and 2-benzyloxyethanol.

<13>

The hair cosmetic composition according to any one of <1> to <9>, wherein component (B) comprises (b3) an organic salt, more preferably a guanidine salt or an arginine salt having a guanidinium group, further preferably at least one selected from guanidine hydrochloride salt, guanidine nitrate salt, guanidine phosphate salt, guanidine thiocyanate salt, guanidine carbonate salt, guanidine acetate salt, guanidine sulfate salt, guanidine sulfamate salt, aminoguanidine hydrochloride salt, aminoguanidine sulfate salt, arginine hydrochloride salt, arginine nitrate salt, arginine phosphate salt, arginine thiocyanate salt, arginine carbonate salt, arginine acetate salt, arginine sulfate salt, arginine sulfamate salt, arginine glutamate salt and arginine aspartate salt, and further preferably guanidine hydrochloride salt.

<14>

The hair cosmetic composition according to any one of <1> to <9>, wherein component (B) preferably comprises a combination of benzyl alcohol and phenethyl alcohol or a combination of benzyl alcohol and ethanol.

<15>

The hair cosmetic composition according to any one of <1> to <14>, wherein the content of component (B) is preferably 6.00% by mass or more, more preferably 7.00% by mass or more, further preferably 10.0% by mass or more, still more preferably 12.0% by mass or more, and yet more preferably 15.0 or more, and preferably 95.0% by mass or less, more preferably 90.0% by mass or less, further preferably 80.0% by mass or less, still more preferably 70.0% by mass or less, and yet more preferably 60.0% by mass or less.

<16>

The hair cosmetic composition according to any one of <1> to <15>, wherein the mass ratio of component (B) to component (A), (B)/(A), is preferably 1 or more, more preferably 5 or more, further preferably 6 or more, still more preferably 7 or more, and preferably 2,000 or less, more preferably 1,000 or less, further preferably 500 or less, and still more preferably 200 or less.

<17>

The hair cosmetic composition according to any one of <1> to <16>, wherein the content of component (C) in the hair cosmetic composition is preferably 10% by mass or more, more preferably 15% by mass or more, and further preferably 20% by mass or more, and preferably 90% by mass or less, more preferably 85% by mass or less, and further preferably 80% by mass or less.

<18>

The hair cosmetic composition according to any one of <1> to <17>, wherein the composition is preferably applied to hair and then dried without being rinsed off.

<19>

A hair cosmetic composition comprising the following components (A) to (C):
  (A) polysilicone-29;
  (B) at least one organic compound selected from an organic compound having a hydrogen bond term of the Hansen solubility parameter of 15.8 MPa$^{1/2}$ or less; and
  (C) water
wherein the content of component (A) is 0.01% by mass or more and 5.00% by mass or less, the content of component (B) is 5.00% by mass or more and 96.77% by mass or less, the mass ratio of component (B) to component (A), (B)/(A), is 1 or more and 200 or less, and the composition has a pH of 1 to 5.

<20>

The hair cosmetic composition according to <19>, wherein component (B) preferably comprises at least one organic compound selected from the group consisting of an aliphatic alcohol having a linear or branched alkyl group having 2 or more and 8 or less carbon atoms and one or more hydroxyl groups, an aromatic alcohol, an ether alcohol, an N-alkylpyrrolidone, an acyclic ester and an alkylamine optionally having a hydroxyl group.

<21>

The hair cosmetic composition according to <20>, wherein component (B) preferably comprises an aromatic alcohol or an ether alcohol.

<22>

The hair cosmetic composition according to <21>, wherein component (B) preferably comprises at least one selected from benzyl alcohol, phenethyl alcohol, phenoxyethanol and 2-benzyloxyethanol.

<23>

The hair cosmetic composition according to <22>, wherein the content of component (B) is preferably 7.00% by mass or more and 95.00% by mass or less.

<24>

A method of use of the hair cosmetic composition according to <23>, wherein the composition is applied to hair and then dried without being rinsed off.

<25>

A hair cosmetic composition comprising the following components (A) to (C):

(A) polysilicone-29;

(B) a guanidine salt; and (C) water, wherein the content of component (A) is 0.01% by mass or more and 5.00% by mass or less, the content of component (B) is 5.00% by mass or more and 96.77% by mass or less, the mass ratio of component (B) to component (A), (B)/(A), is 1 or more and 200 or less, and the composition has a pH of 1 to 5.

<26>

The hair cosmetic composition according to <25>, wherein the content of component (B) is preferably 7.00% by mass or more and 95.00% by mass or less.

<27>

The hair cosmetic composition according to <26>, wherein the mass ratio of component (B) to component (A), (B)/(A), is preferably 1.67 to 120 or less.

<28>

The hair cosmetic composition according to <27>, wherein the guanidine salt is at least one selected from guanidine hydrochloride salt, guanidine nitrate salt, guanidine phosphate salt, a guanidine thiocyanate salt, guanidine carbonate salt, guanidine acetate salt, guanidine sulfate salt, guanidine sulfamate salt, aminoguanidine hydrochloride salt and aminoguanidine sulfate salt.

<29>

A method of using the hair cosmetic composition according to <28>, comprising applying the composition to hair and then drying without rinsing off.

<30>

Use of the hair cosmetic composition according to any one of <1> to <23> and <25> to <28> for giving hydrophobicity to hair and lowering friction of hair.

Examples

Test Example 1 Measurement of Effect of Inhibiting Formation of Micelles

The critical micelle concentration (CMC) in the case where different types of compounds were added to an aqueous solution of polyether modified silicone was measured by the method described above. The results are shown in Table 1.

TABLE 1

| | Compound added | Amount added (% by mass) | CMC of aqueous solution*3 (% by mass) | $\delta^{*1}$ $(MPa^{1/2})$ | Effect of inhibiting formation of micelles*2 |
|---|---|---|---|---|---|
| | No additives | — | 0.13 | 42.3 | — |
| (b2) | Ethanol | 10 | 0.21 | 17.6 | Inhibited |
| (b1) | Phenoxyethanol | 1 | 0.22 | 12.2 | |
| (b1) | Benzyl alcohol | 1 | 0.21 | 12.4 | |
| (b1) | 2-phenyl-1-propanol | 1 | 0.24 | 10.2 | |
| (b1) | 2-propanol | 10 | 0.35 | 14.3 | |
| (b1) | N-(2-hydroxyethyl)-2-pyrrolidone | 10 | 0.36 | 13.5 | |
| (b1) | Ethyl lactate | 10 | 0.36 | 14.4 | |
| (b2) | Diethanolamine | 10 | 0.2 | 20.3 | |
| (b3) | Guanidine hydrochloride | 10 | 0.25 | — | |
| | Propylene glycol | 10 | 0.13 | 21.7 | Not inhibited |
| | Glycerol | 10 | 0.12 | 29.3 | |
| | Glucose | 10 | 0.13 | — | |
| | Erythritol | 10 | 0.115 | — | |

*1Hydrogen bond term of the Hansen solubility parameter
*2The amount of CMC of more than 0.13% by mass were determined as having the effect of inhibiting formation of micelles.
*3Aqueous solution wherein a compound was added to an aqueous solution of polyether modified silicone As shown in Table 1, ethanol, diethanolamine and guanidine hydrochloride had the effect of inhibiting formation of micelles, in addition to the compounds having a hydrogen bond term of the Hansen solubility parameter of 10.0 $MPa^{1/2}$ or more and 15.8 $MPa^{1/2}$ or less.

Examples 1 to 15, Comparative Examples 1 to 10

Aqueous solutions (hair cosmetic compositions) having the composition shown in Tables 2 to 4 were prepared, and the advancing contact angle of the hair treated with these aqueous solutions with water and combing force of the hair were measured, and various sensory evaluations were performed.

The pH in the tables was directly measured without, for example, diluting the composition, at room temperature (25° C.) by using a pH meter F-52 manufactured by HORIBA, Ltd.

(Method of Producing Each Aqueous Solution)

A predetermined amount shown in the tables of distilled water and the respective components were weighed in a 200 mL beaker in which a stirring bar was placed, then mixed and stirred at 300 rpm using a slim stirrer (manufactured by As One Corporation) for 12 hours or more until being homogeneous.

(Method of Treatment)

Damaged hair prepared by bleaching a 5.0-g hair tress of the hair from a healthy Japanese once and repeating shampooing 360 times was used as the hair for evaluation in all cases.

The aqueous solution produced in the respective Examples and Comparative Examples was applied to hair at the bath ratio shown in the tables (the hair was dipped in the aqueous solution in Comparative Example 9), and then the hair was thoroughly dried without rinsing using a hair dryer. Those in which the hair was then washed once using the plain shampoo described below and dried was referred to as after shampooing once and those in which washing and drying was repeated 20 times were referred to as after shampooing 20 times.

In Comparative Example 6, the hair prepared by washing untreated damage hair once using the plain shampoo and then drying was used for evaluation (evaluation after shampooing 20 times was not performed).

| Composition of plain shampoo (pH 6.9) | (% by mass) |
|---|---|
| Sodium polyoxyethylene lauryl ether sulfate (EMAL 170J manufactured by Kao Corporation, 70% by mass of active ingredient) | 13.0 |
| Coconut oil fatty acid monoethanolamide (AMISOL CME manufactured by Kawaken Fine Chemicals Co., Ltd.) | 0.6 |
| Coconut oil fatty acid amidopropylcarbobetaine (AMPHITOL 55AB manufactured by Kao Corporation, 30% by mass of active ingredient) | 1.41 |
| Citric acid | in amount to adjust pH |
| Sodium benzoate | 0.3 |
| Purified water | Balance |

(Advancing Contact Angle of Hair)

The advancing contact angle of hair with water was measured and determined as the value of contact angle. The advancing contact angle was measured using distilled water and a measurement apparatus, Processor Tensiometer K100 manufactured by KRUSS GmbH under conditions of a surface tension of water: 72.8 mN/m, a density of water: 0.990 g/cm$^3$, a maximum immersion depth: 4 mm, a minimum immersion depth: 1 mm and a measurement speed: 2 mm/min. 5 hairs were collected from a hair tress which had been treated by the respective treatments, and the portion 5 cm from the root was used for the measurement. The average value of the five hairs was determined as the value of the contact angle. When the value is more than 90°, a higher value indicates that the hair is more hydrophobic. When the value is less than 90°, a lower value indicates that the hair is more hydrophilic. In short, a higher value of more than 90° indicates that the treatment successfully gives excellent hydrophobicity.

(Combing Force)

The combing force of hair after rinsing with warm water at 40° C. for 15 seconds was measured by the dynamic combing force method (Suzuki, et. al., J. Soc. Cosmet. Chem. Japan. Vol. 27, No. 1, P11-13 1993). The average of 10 measured values was employed. A smaller value indicates that combability is better and the hair is smoother.

(Sensory Evaluation)

The items of "easy detangling of tress in drying step," "good finger combability during drying," "little stickiness of hair to fingers after drying," and "quick drying of hair" were evaluated by 7 expert panelists. The compositions were evaluated by each of the panelists on a scale of "5: Excellent" to "1: Bad" with the condition of healthy hair before bleaching and shampooing as "5: Excellent." The evaluation was conducted using the total score.

TABLE 2

| | | | Example | | | | | | | Comparative Example | | | | | |
|---|---|---|---|---|---|---|---|---|---|---|---|---|---|---|---|
| | Content (% by mass, active amount for all) | | 1 | 2 | 3 | 4 | 5 | 6 | 7 | 1 | 2 | 3 | 4 | 5 | 6(*5) |
| (A) | | Epoxyaminosilane copolymer (*4) | 1 | 1 | 1 | 1 | 1 | 1 | 1 | 1 | 1 | 1 | 1 | 1 | — |
| (B) | (b2) | Ethanol | 10 | 8 | 8 | 8 | — | — | — | — | — | — | — | — | — |
| | (b1) | Benzyl alcohol | — | 2 | — | — | — | — | — | — | — | — | — | — | — |
| | (b1) | Phenoxyethanol | — | — | 2 | — | — | — | — | — | — | — | — | — | — |
| | (b1) | 2-phenyl-1-propanol | — | — | — | 2 | — | — | — | — | — | — | — | — | — |
| | (b1) | Ethyl lactate | — | — | — | — | 10 | — | — | — | — | — | — | — | — |
| | (b2) | Diethanolamine | — | — | — | — | — | 10 | — | — | — | — | — | — | — |
| | (b3) | Guanidine hydrochloride | — | — | — | — | — | — | 10 | — | — | — | — | — | — |
| (B') | | Propylene glycol | — | — | — | — | — | — | — | — | 10 | — | — | — | — |
| | | Glycerol | — | — | — | — | — | — | — | — | — | 10 | — | — | — |
| | | Glucose | — | — | — | — | — | — | — | — | — | — | 10 | — | — |
| | | Erythritol | — | — | — | — | — | — | — | — | — | — | — | 10 | — |
| (C) | | Water (*6) | 89 | 89 | 89 | 89 | 89 | 89 | 89 | 99 | 89 | 89 | 89 | 89 | — |
| Others | | Lactic acid | *7 | *7 | *7 | *7 | *7 | *7 | *7 | | *7 | *7 | *7 | *7 | *7 | — |
| pH | | | 3.5 | 3.5 | 3.5 | 3.5 | 3.5 | 3.5 | 3.5 | 3.5 | 3.5 | 3.5 | 3.5 | 3.5 | — |
| Total amount | | | 100 | 100 | 100 | 100 | 100 | 100 | 100 | 100 | 100 | 100 | 100 | 100 | — |
| Mass ratio (B)/(A) or (B')/(A) | | | 10 | 10 | 10 | 10 | 10 | 10 | 10 | 0 | 10 | 10 | 10 | 10 | — |
| Treatment bath ratio (aqueous solution/hair) | | | 0.5 | 0.5 | 0.5 | 0.5 | 0.5 | 0.5 | 0.5 | 0.5 | 0.5 | 0.5 | 0.5 | 0.5 | — |
| Advancing contact angle (°) | (After shampooing once) | | 124 | 126 | 127 | 128 | 129 | 123 | 121 | 116 | 108 | 99 | 102 | 100 | 59 |
| | (After shampooing 20 times) | | 99 | 102 | 102 | 105 | 105 | 99 | 96 | 79 | 71 | 69 | 70 | 68 | — |
| Combing force | (After shampooing once) | | 198 | 184 | 178 | 178 | 176 | 195 | 207 | 366 | 403 | 440 | 437 | 433 | 728 |
| | (After shampooing 20 times) | | 226 | 210 | 209 | 210 | 202 | 230 | 238 | 626 | 648 | 679 | 668 | 670 | — |
| Functional Evaluation (After shampooing once) | Easy detangling of tress in drying step | | 26 | 27 | 27 | 27 | 25 | 24 | 29 | 20 | 20 | 18 | 20 | 19 | 7 |
| | Good finger combability during drying | | 32 | 34 | 33 | 33 | 30 | 30 | 30 | 20 | 20 | 18 | 20 | 19 | 7 |
| | Little stickiness of hair to fingers after drying | | 31 | 33 | 33 | 34 | 27 | 25 | 27 | 16 | 15 | 14 | 14 | 14 | 22 |
| | Quick drying of hair | | 27 | 27 | 26 | 28 | 25 | 25 | 27 | 15 | 16 | 14 | 17 | 15 | 7 |

TABLE 2-continued

|  | Content (% by mass, active amount for all) | Example 1 | 2 | 3 | 4 | 5 | 6 | 7 | Comparative Example 1 | 2 | 3 | 4 | 5 | 6(*5) |
|---|---|---|---|---|---|---|---|---|---|---|---|---|---|---|
| Functional Evaluation (After shampooing 20 times) | Easy detangling of tress in drying step | 25 | 26 | 26 | 27 | 25 | 25 | 29 | 15 | 16 | 14 | 15 | 14 | 7 |
|  | Good finger combability during drying | 26 | 29 | 30 | 30 | 29 | 28 | 27 | 12 | 13 | 10 | 12 | 11 | 7 |
|  | Little stickiness of hair to fingers after drying | 29 | 30 | 30 | 31 | 27 | 25 | 27 | 15 | 16 | 10 | 14 | 13 | 22 |
|  | Quick drying of hair | 24 | 26 | 26 | 26 | 27 | 23 | 24 | 13 | 16 | 11 | 13 | 12 | 7 |

(*4) Silsoft CLX-E (Polysilicone-29 manufactured by Momentive Performance Materials, 15% by mass)

(*5) Untreated damaged hair (*6) Including water and dipropylene glycol derived from Silsoft CLX-E

*7 In amount to adjust pH

TABLE 3

|  |  | Content (% by mass, active amount for all) | Example 8 | 9 | 10 | 11 | 12 | 13 | 14 | 15 | Comparative Example 7 | 8 |
|---|---|---|---|---|---|---|---|---|---|---|---|---|
| (A) |  | Epoxyaminosilane copolymer (*4) | 0.1 | 0.5 | 5 | 1 | 1 | 1 | 1 | 1 | 1 | 1 |
| (B) | (b2) | Ethanol | 10 | 10 | 10 | 5 | 7 | 20 | 93.3 | 20 | 3 | — |
|  | (b1) | Benzyl alcohol | — | — | — | — | — | — | — | 2 | — | 2 |
|  | (b1) | Phenoxyethanol | — | — | — | — | — | — | — | 2 | — | — |
| (C) |  | Water (*6) | 89.9 | 89.5 | 85 | 94 | 92 | 79 | 5.7 | 75 | 96 | 97 |
| Others |  | Lactic acid | *7 | *7 | *7 | *7 | *7 | *7 | *7 | *7 | *7 | *7 |
| pH |  |  | 3.5 | 3.5 | 3.5 | 3.5 | 3.5 | 3.5 | 3.5 | 3.5 | 3.5 | 3.5 |
| Total amount |  |  | 100 | 100 | 100 | 100 | 100 | 100 | 100 | 100 | 100 | 100 |
| Mass ratio (B)/(A) |  |  | 100 | 20 | 2 | 5 | 7 | 20 | 93.5 | 24 | 3 | 2 |
| Treatment bath ratio (aqueous solution/hair) |  |  | 0.5 | 0.5 | 0.5 | 0.5 | 0.5 | 0.5 | 0.5 | 0.5 | 0.5 | 0.5 |
| Advancing contact angle (°) | (After shampooing once) |  | 112 | 122 | 133 | 109 | 118 | 130 | 136 | 132 | 117 | 116 |
|  | (After shampooing 20 times) |  | 92 | 97 | 119 | 91 | 96 | 106 | 118 | 111 | 77 | 71 |
| Combing force | (After shampooing once) |  | 246 | 211 | 198 | 253 | 233 | 167 | 158 | 157 | 333 | 342 |
|  | (After shampooing 20 times) |  | 282 | 243 | 211 | 289 | 247 | 192 | 172 | 186 | 611 | 692 |
| Functional Evaluation (After shampooing once) | Easy detangling of tress in drying step |  | 22 | 25 | 32 | 23 | 27 | 29 | 33 | 33 | 24 | 22 |
|  | Good finger combability during drying |  | 28 | 30 | 32 | 28 | 29 | 29 | 34 | 35 | 23 | 21 |
|  | Little stickiness of hair to fingers after drying |  | 23 | 26 | 27 | 23 | 27 | 30 | 32 | 33 | 22 | 21 |
|  | Quick drying of hair |  | 25 | 36 | 31 | 25 | 28 | 30 | 31 | 32 | 22 | 21 |
| Functional Evaluation (After shampooing 20 times) | Easy detangling of tress in drying step |  | 22 | 24 | 30 | 23 | 25 | 28 | 30 | 33 | 13 | 133 |
|  | Good finger combability during drying |  | 27 | 27 | 30 | 27 | 29 | 29 | 31 | 34 | 15 | 14 |
|  | Little stickiness of hair to fingers after drying |  | 24 | 25 | 24 | 25 | 27 | 28 | 29 | 32 | 21 | 21 |
|  | Quick drying of hair |  | 24 | 25 | 28 | 25 | 27 | 27 | 27 | 31 | 14 | 13 |

(*4) Silsoft CLX-E (Polysilicone-29 manufactured by Momentive Performance Materials, 15% by mass)

(*6) Including water and dipropylene glycol derived from Silsoft CLX-E

*7 In amount to adjust pH

TABLE 4

|  |  |  | Comparative Example | |
|---|---|---|---|---|
| Content (% by mass, active amount for all) | | | 9 | 10 |
| (A) | Epoxyaminosilane copolymer (*4) | | 1 | — |
| (A') | Aminosilicone polyether copolymer (*8) | | — | 1 |
| (B) | (b2) | Ethanol | — | 10 |
| (C) | | Water (*9) | 99 | 89 |
| Others | | Lactic acid | *7 | *7 |
| | | pH | 3.5 | 3.5 |
| Total amount | | | 100 | 100 |
| Mass ratio (B)/(A) or (B)/(A') | | | 0 | 10 |
| Treatment bath ratio (aqueous solution/hair) | | | 25 | 0.5 |
| Advancing contact angle (°) | After shampooing once | | 121 | 65 |
| | After shampooing 20 times | | 104 | 60 |
| Combing force | After shampooing once | | 246 | 678 |
| | After shampooing 20 times | | 299 | 711 |
| Sensory Evaluation (After shampooing once) | Easy detangling of tress in drying step | | 28 | 8 |
| | Good finger combability during drying | | 29 | 8 |
| | Little stickiness of hair to fingers after drying | | 12 | 23 |
| | Quick drying of hair | | 10 | 9 |
| Sensory Evaluation (After shampooing 20 times) | Easy detangling of tress in drying step | | 29 | 7 |
| | Good finger combability during drying | | 24 | 7 |
| | Little stickiness of hair to fingers after drying | | 12 | 22 |
| | Quick drying of hair | | 9 | 7 |

(*4) Silsoft CLX-E (Polysilicone-29 manufactured by Momentive Performance Materials, 15% by mass)
*7 In amount to adjust pH
(*8) Silsoft A+ (PEG-40/PPG-8 methylaminopropyl/hydroxypropyl dimethicone copolymer manufactured by Momentive Performance Materials, 30% by mass)
(*9) Including water and dipropylene glycol derived from Silsoft CLX-E, and water derived from Silsoft A+

Formulation Example 1 (Leave-in Hair Lotion) by Mass, Active Amount for all)

| | |
|---|---|
| Epoxyaminosilane copolymer (Silsoft CLX-E manufactured by Momentive Performance Materials was used, 15% by mass of active amount) | 1.0 |
| Ethanol | 25.0 |
| Hydroxyethyl cellulose (SE-850 manufactured by DAICEL FINECHEM Ltd.) | 0.05 |
| Lactic acid | in amount to adjust pH |
| Water | Balance (*6) pH 3.5 |

(*6): Including water and dipropylene glycol derived from Silsoft CLX-E

| | |
|---|---|
| Epoxyaminosilane copolymer (Silsoft CLX-E manufactured by Momentive Performance Materials was used, 15% by mass of active amount) | 1.0 |
| Ethanol | 20.0 |
| Benzyl alcohol | 5.0 |
| Phenoxyethanol | 2.0 |
| Lactic acid | in amount to adjust pH |
| Water | Balance (*6) pH 3.5 |

(*6): Including water and dipropylene glycol derived from Silsoft CLX-E

Formulation Example 3 (Leave-in Hair Lotion) by Mass, Active Amount for all)

| | |
|---|---|
| Epoxyaminosilane copolymer (Silsoft CLX-E manufactured by Momentive Performance Materials was used, 15% by mass of active amount) | 1.0 |
| Ethanol | 25.0 |
| Polyquaternium-37 (Cosmedia Ultragel 300 manufactured by BASF) | 0.25 |
| Lactic acid | in amount to adjust pH |
| Water | Balance (*6) pH 3.5 |

(*6): Including water and dipropylene glycol derived from Silsoft CLX-E

The invention claimed is:

1. A hair cosmetic composition comprising the following components (A) to (C), wherein a content of component (A) is 0.2% by mass to 2.00% by mass, a content of component (B) is 15% by mass to 95% by mass, and a mass ratio of component (B) to component (A), (B)/(A), is 20 to 93.5:
   (A) polysilicone-29;
   (B) ethanol; and
   (C) water,
   wherein the hair cosmetic composition has a pH of 1.0 to 4.0.

2. The hair cosmetic composition according to claim 1, which is applied to hair and then dried without being rinsed off.

3. A hair cosmetic composition comprising the following components (A) to (C):
   (A) polysilicone-29;
   (B) ethanol; and
   (C) water,
   wherein a content of component (A) is 0.2% by mass to 2.00% by mass, a content of component (B) is 15% by mass to 95% by mass, a mass ratio of component (B) to component (A), (B)/(A), is 20 to 93.5, and the composition has a pH of 1.0 to 4.0.

* * * * *